(12) United States Patent
Frison et al.

(10) Patent No.: US 11,181,752 B2
(45) Date of Patent: Nov. 23, 2021

(54) LENS FOR ASTIGMATISM

(71) Applicant: SIFI MEDTECH S. P. A., Aci Sant' Antonio (IT)

(72) Inventors: Renato Frison, Chions (IT); Maria Cristina Curatolo, Aci Sant' Antonio (IT)

(*) Notice: Subject to any disclaimer, the term of this patent is extended or adjusted under 35 U.S.C. 154(b) by 56 days.

(21) Appl. No.: 16/336,165

(22) PCT Filed: Sep. 29, 2017

(86) PCT No.: PCT/IB2017/055996
§ 371 (c)(1),
(2) Date: Mar. 25, 2019

(87) PCT Pub. No.: WO2018/060940
PCT Pub. Date: Apr. 5, 2018

(65) Prior Publication Data
US 2019/0243162 A1 Aug. 8, 2019

(30) Foreign Application Priority Data

Sep. 29, 2016 (IT) .................. 102016000097763

(51) Int. Cl.
*G02C 7/02* (2006.01)
*A61F 2/16* (2006.01)

(52) U.S. Cl.
CPC ............ *G02C 7/028* (2013.01); *A61F 2/1618* (2013.01); *A61F 2/1645* (2015.04); *G02C 7/02* (2013.01); *A61F 2/1613* (2013.01); *G02C 2202/02* (2013.01)

(58) Field of Classification Search
CPC .......... G02C 7/02; G02C 7/028; G02C 7/047; G02C 7/027; G02C 7/049; G02C 2202/02; A61B 3/125; A61B 3/1015; A61B 3/107; A61F 2/1645; A61F 2/1618; A61F 2/1613; A61F 2/16
USPC ............ 351/159.54, 159.72, 159.74, 159.76, 351/159.73, 178, 219, 246
See application file for complete search history.

(56) References Cited

U.S. PATENT DOCUMENTS

| 2008/0013043 A1* | 1/2008 | Ye ..................... G02C 7/028 351/159.2 |
| 2009/0323020 A1 | 12/2009 | Zhao et al. |
| 2013/0222761 A1* | 8/2013 | Hansen ............... G02C 7/045 351/159.13 |

FOREIGN PATENT DOCUMENTS

| EP | 2634619 A1 | 9/2013 |
| WO | 2012154597 A1 | 11/2012 |

OTHER PUBLICATIONS

International Search Report and Written Opinion dated Jan. 22, 2018 for corresponding PCT patent application No. PCT/IB2017/055996.

(Continued)

*Primary Examiner* — Jie Lei
(74) *Attorney, Agent, or Firm* — Abelman, Frayne & Schwab; Stefan Knirr

(57) ABSTRACT

A lens for correcting astigmatism, possibly of ocular type, shaped so as to reduce the aberrations caused by accidental displacements with respect to the ideal correction position, in particular so as to ensure satisfactory performance even when rotated with respect to the ideal axis thereof.

2 Claims, 18 Drawing Sheets

(56) References Cited

OTHER PUBLICATIONS

International Preliminary Report on Patentability dated Dec. 10, 2018 for corresponding PCT patent application No. PCT/IB2017/055996.

* cited by examiner

LENS FOR ASTIGMATISM

CROSS REFERENCE TO RELATED APPLICATIONS

This application is a national phase of PCT application No. PCT/IB2017/055996, filed Sep. 29, 2017, which claims priority to IT patent application No. 102016000097763, filed Sep. 29, 2016, all of which are incorporated herein by reference thereto.

FIELD OF THE INVENTION

The present invention relates to a corrective lens for astigmatism, and more particularly to a corrective lens having an advantageous behavior even when rotated with respect to the ideal axis thereof.

BACKGROUND ART

Astigmatism is a refractive optical defect in which the vision has deteriorated. Astigmatism can derive from the cornea, the crystalline lens or both, and can be caused by an irregular, non-symmetrical corneal curvature. An astigmatic cornea is more curved in one direction rather than another, and this results in an incorrect focusing of a point which appears elongated instead of punctiform.

Corneal astigmatism can be corrected by means of laser surgery or toric corrective lenses in the shape of eye-glasses, contact lenses and intraocular lenses. Surgical correction can be done to correct astigmatism and decrease or eliminate dependency on glasses or contact lenses. Such a surgery can include the implantation of an intraocular lens after cataract removal surgery.

Figure 1A:
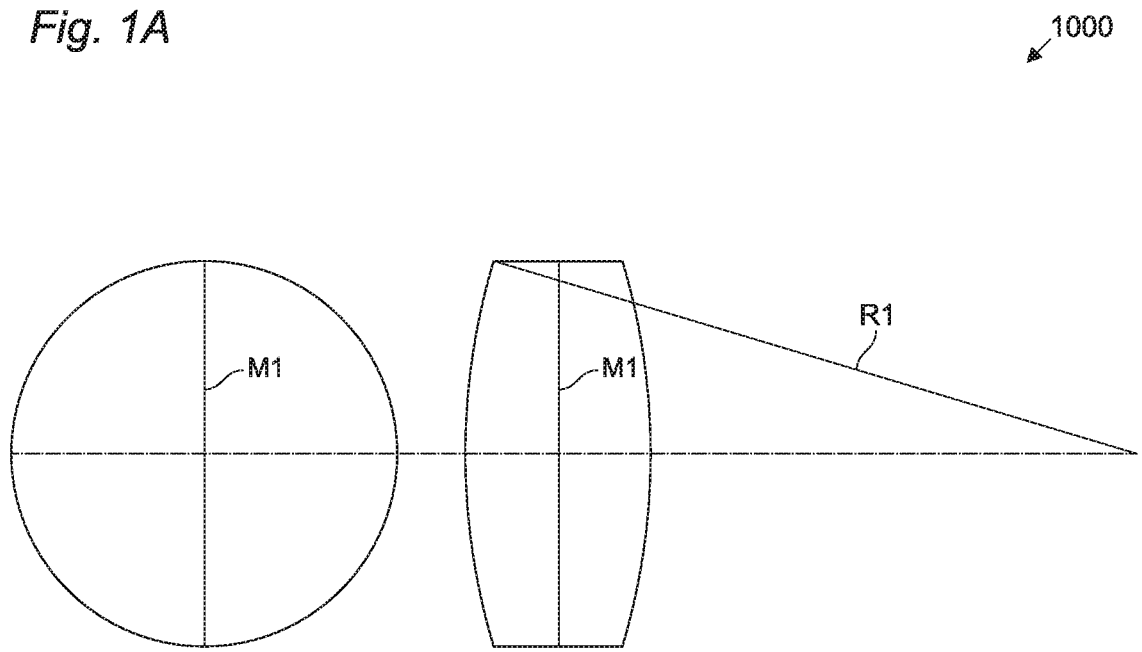
Figure 1A:
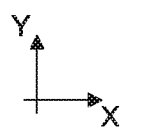
Figure 1A:
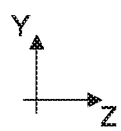
Figure 1B:
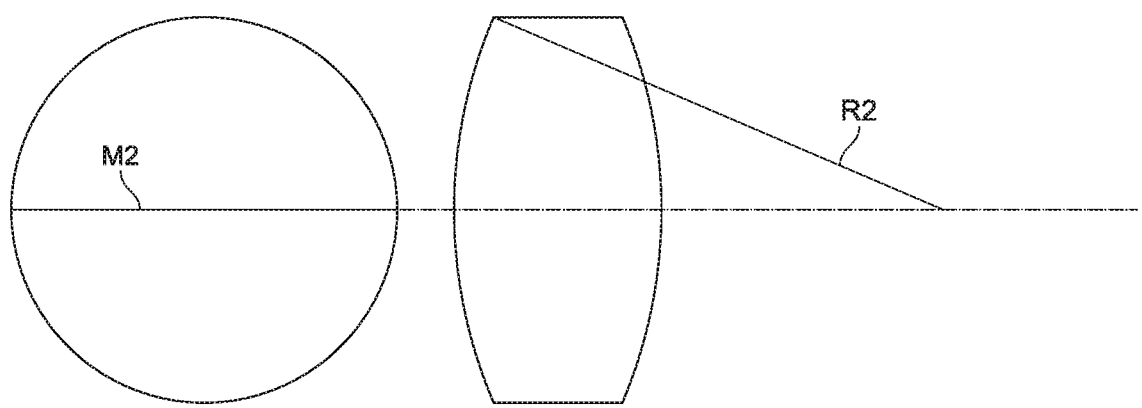
Figure 1B:
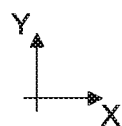
Figure 1B:
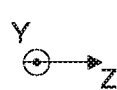

A toric lens 1000 according to the prior art is diagrammatically shown in FIGS. 1A and 1B. In particular, the toric lens 1000 has optics with two different powers with respect to two meridians M1 and M2 oriented perpendicularly. In other words, two curvature radii R1 and R2 coexist in the same lens 1000, the first being flatter and the second more curved, with the function of correcting the focus defect given by the difference in power in the two meridians of the astigmatic cornea.

Each eye with astigmatism requires a specific position of the two meridians M1 and M2 of the lens with respect to the eye in order to correct astigmatism. In other words, the angle formed by meridian M1 with the vertical direction Y is specific for each eye. When the lens rotates around the optical axis Z, the correction effectiveness is quickly deteriorated. Such a deterioration is enhanced if lens 1000 is also multifocal, for example.

It is therefore important that lens 1000 does not rotate with respect to axis Z. This can be easily achieved in the case of glasses where the lens is kept in a fixed position by the frame. On the contrary, in the case of contact lenses or intraocular lenses, keeping the lens in a specific position is more difficult.

Some toric intraocular lenses include a particular mechanical design to prevent rotation. For example, intraocular lenses with a biscuit-like design or lenses with four loops to ensure stability in the capsule are known.

Some toric lenses have modified optics, in particular by modifying the power shape or the orientation of the meridians. However, these solutions also have drawbacks. In general, in each of these solutions, an increase in the vision quality for high angular rotations corresponds to a deterioration of the vision quality at low values of angular separation.

SUMMARY OF THE INVENTION

It is therefore an object of the present invention to provide a lens, possibly of the intraocular type, capable of reducing the aberrations caused by a rotation with respect to the ideal correction position.

It is another object of the present invention to provide a lens which corresponds to a continuous surface, little deformed and therefore easy to be implemented.

Such objects are achieved by a lens according to the independent claim.

In particular, the inventors have developed a lens with an optical design modified by a corrective term which makes the system more tolerant to the rotation of the lens itself.

In particular, an embodiment of the present invention may relate to a lens for correcting astigmatism having a correcting factor modulated by the equation $Cos[2\theta] \cdot Sin[2\alpha]$, where $\theta$ indicates the position, with respect to a reference meridian, of a radius or a meridian to which the correction is applied, where $\alpha$ indicates a misalignment angle of the lens with respect to an ideal correction angle of the astigmatism.

Due to this implementation, it is advantageously possible to obtain a more tolerant lens with respect to the deterioration introduced by a rotation.

In some embodiments, the lens may comprise at least a first part and a second part, wherein at least the first part has a correction factor modulated by the equation $Cos[2\theta] \cdot Sin[2\alpha]$ and where at least the second part has a correction factor modulated by the equation $Cos[2\theta] \cdot Sin[-2\alpha]$.

Due to this implementation, it is advantageously possible to obtain a more tolerant lens with respect to the possible misalignments α in both positive and negative directions.

In some embodiments, the first part and the second part may have a substantially similar dimension.

Due to this implementation, it is advantageously possible to obtain a substantially symmetrical behavior of the lens for positive and negative rotation values.

In some embodiments, the lens may comprise a plurality of first parts and a plurality of second parts.

Due to this implementation, it is advantageously possible to implement a division of the lens in more than two parts, for example for reasons related to the production of the lens itself.

In some embodiments, the lens may be a toric lens.

Due to this implementation, it is advantageously possible to use the lens to correct astigmatism.

In some embodiments, the correcting factor may be obtained by introducing a deformation on a surface of the lens, consisting of a linear combination of Zernike polynoms $Z_4$ and $Z_5$.

Due to this implementation, it is possible to obtain the required correction using an appropriate combination of polynoms.

BRIEF LIST OF DRAWINGS

Further features and advantages of the invention will become more apparent from the following detailed description of preferred but non-exclusive embodiments, shown by way of non-limiting example with the aid of the accompanying drawings. In the drawings, the same reference numerals identify the same components.

Figure 2:
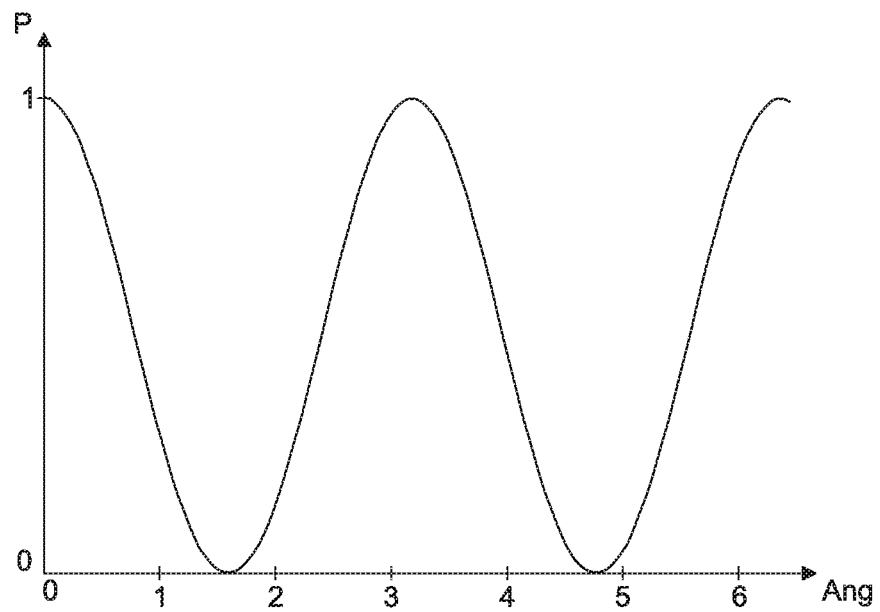
Figure 3:
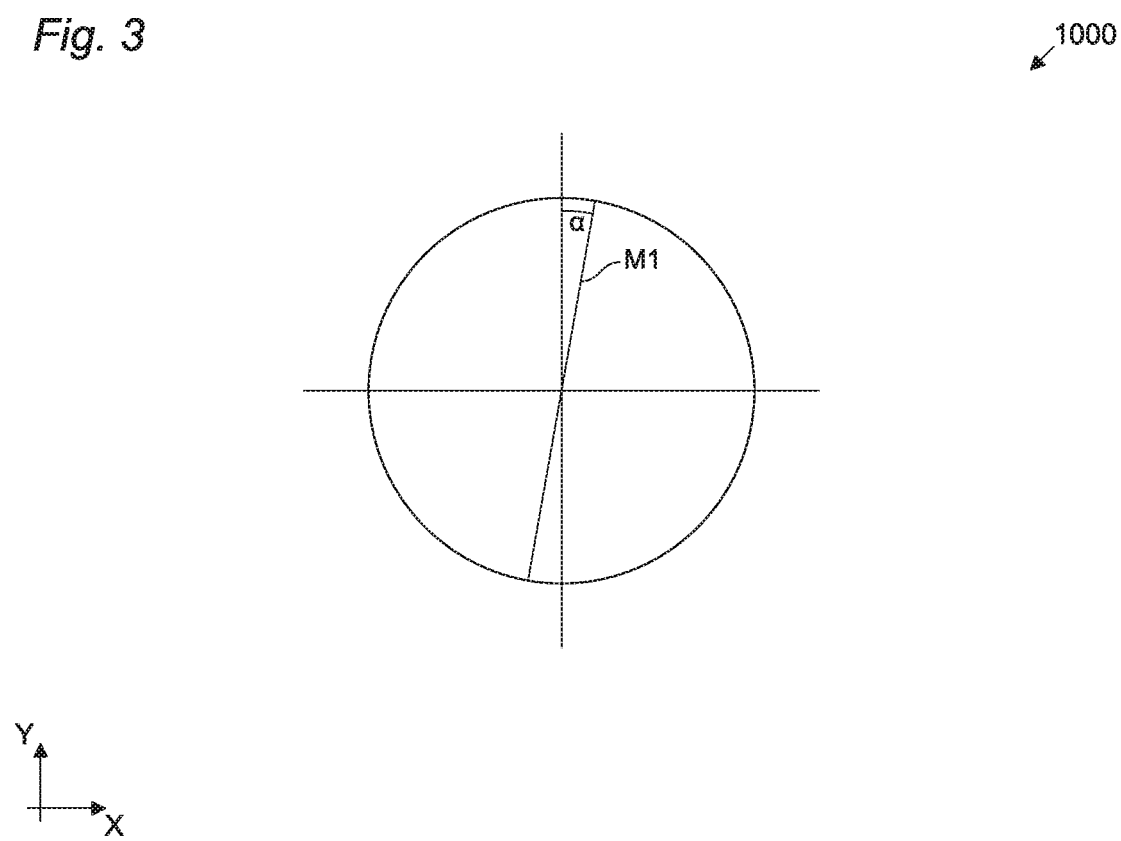
Figure 4:
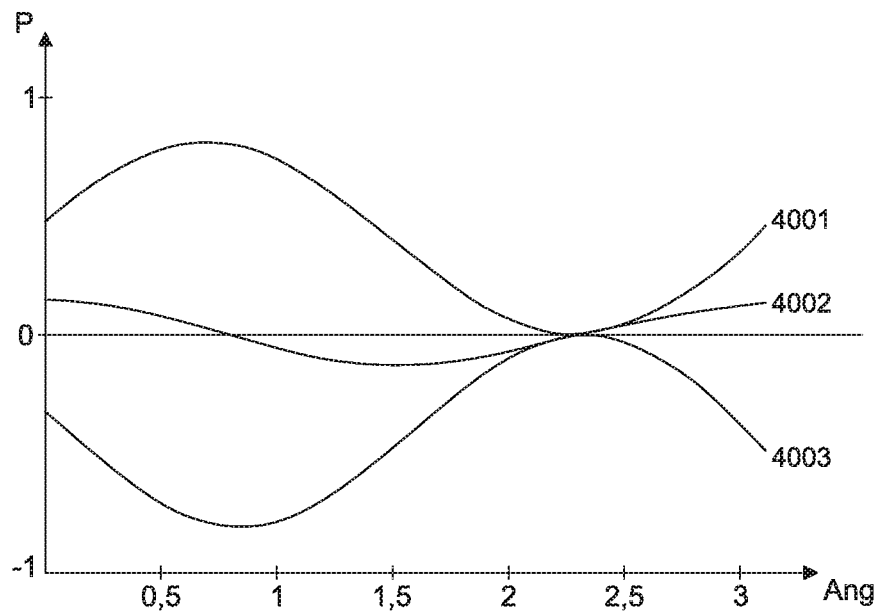
Figure 6:
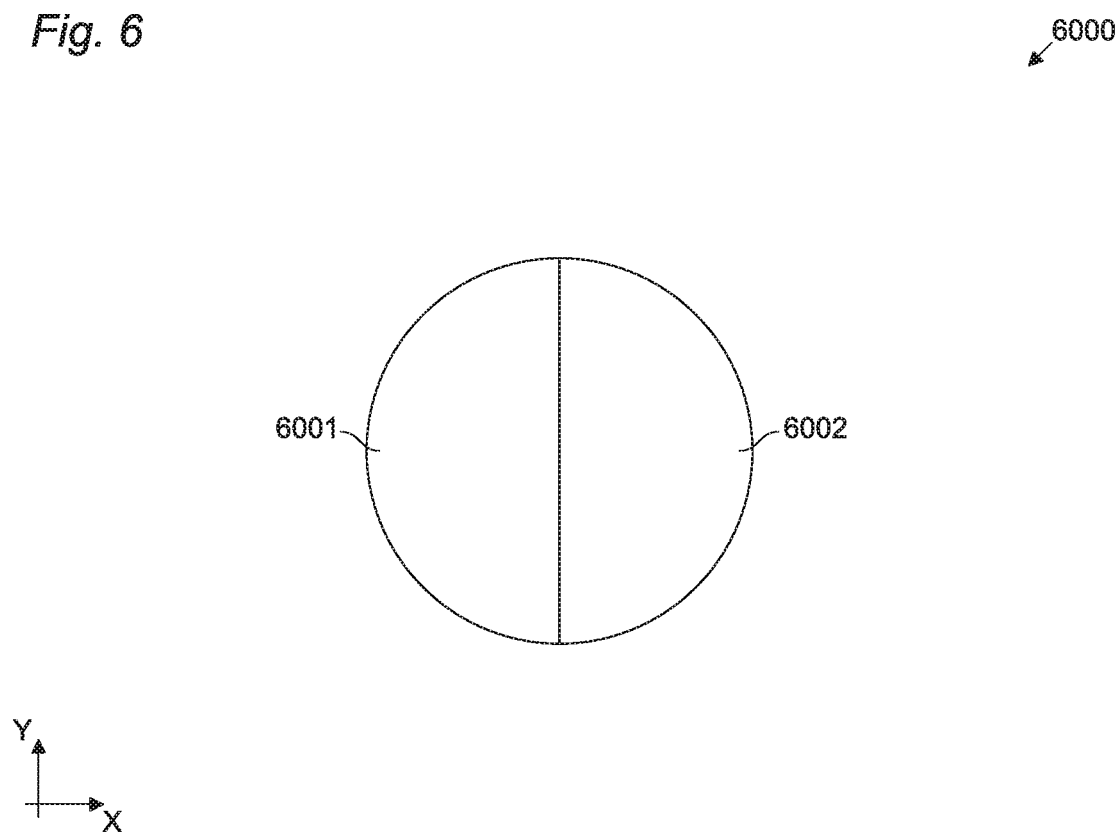
Figure 7A:
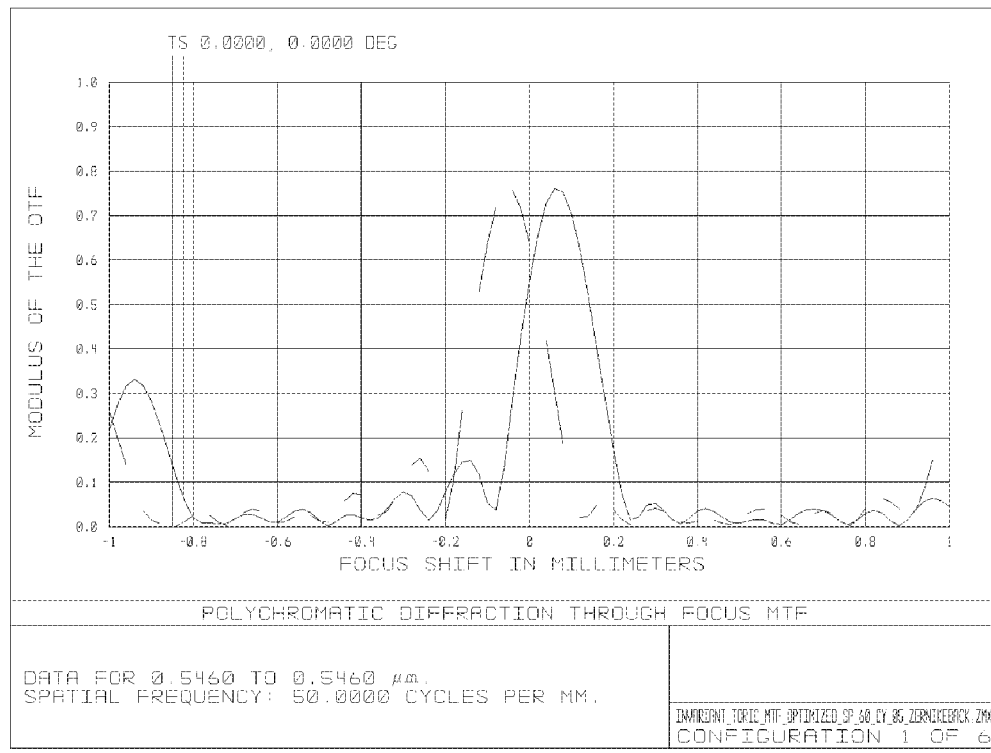
Figure 7B:
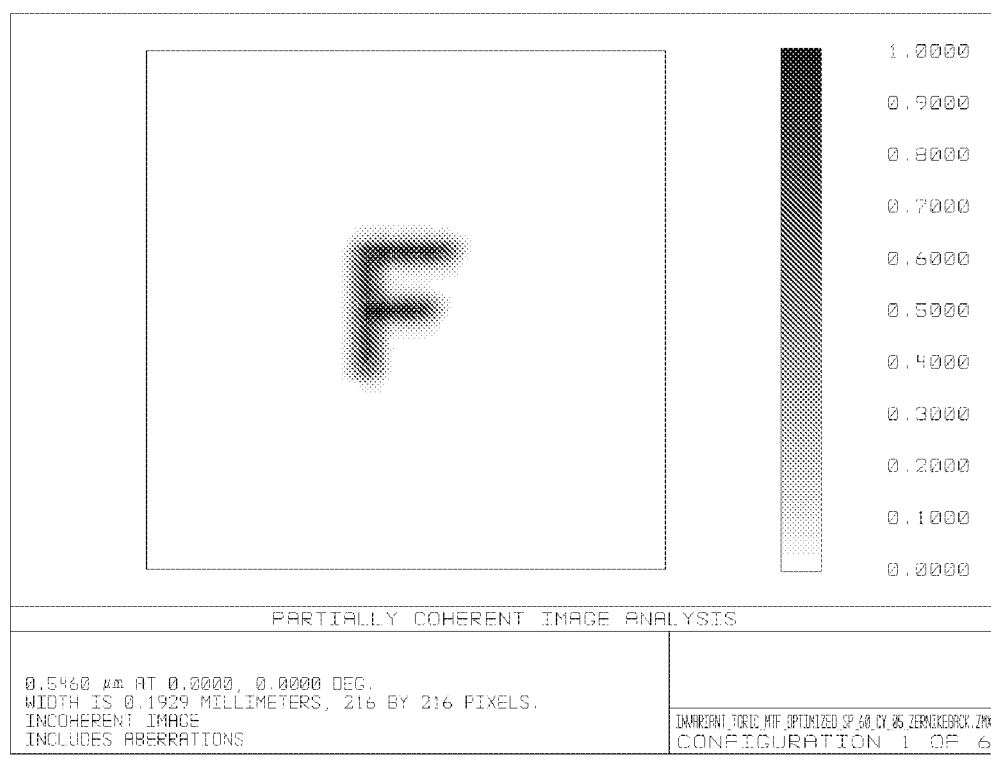
Figure 7C:
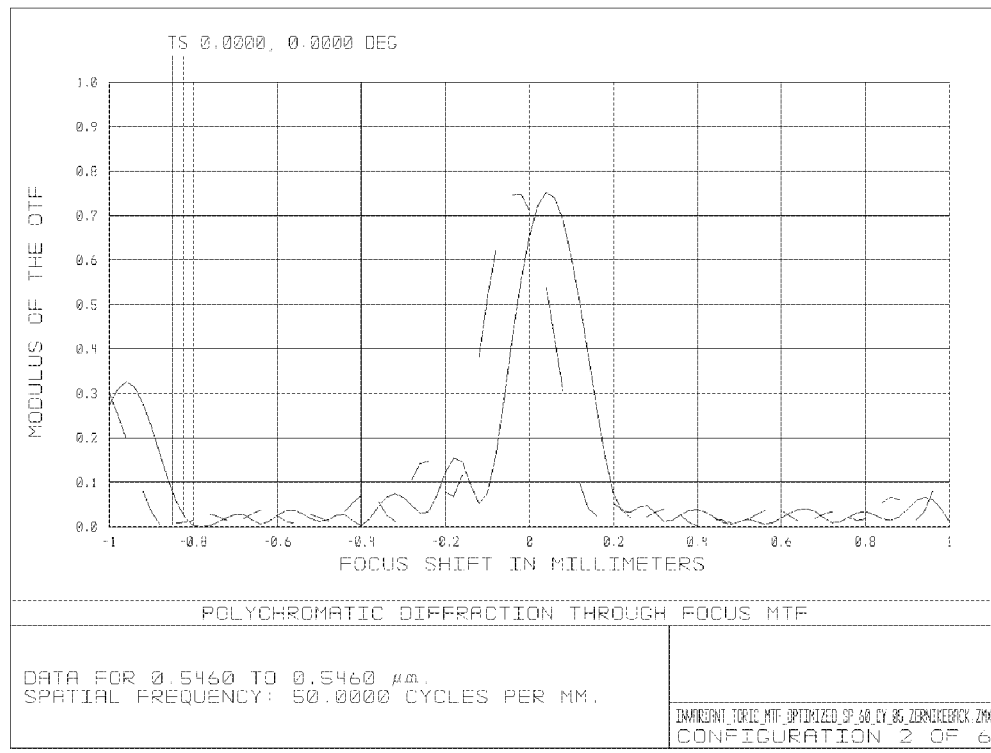
Figure 7D:
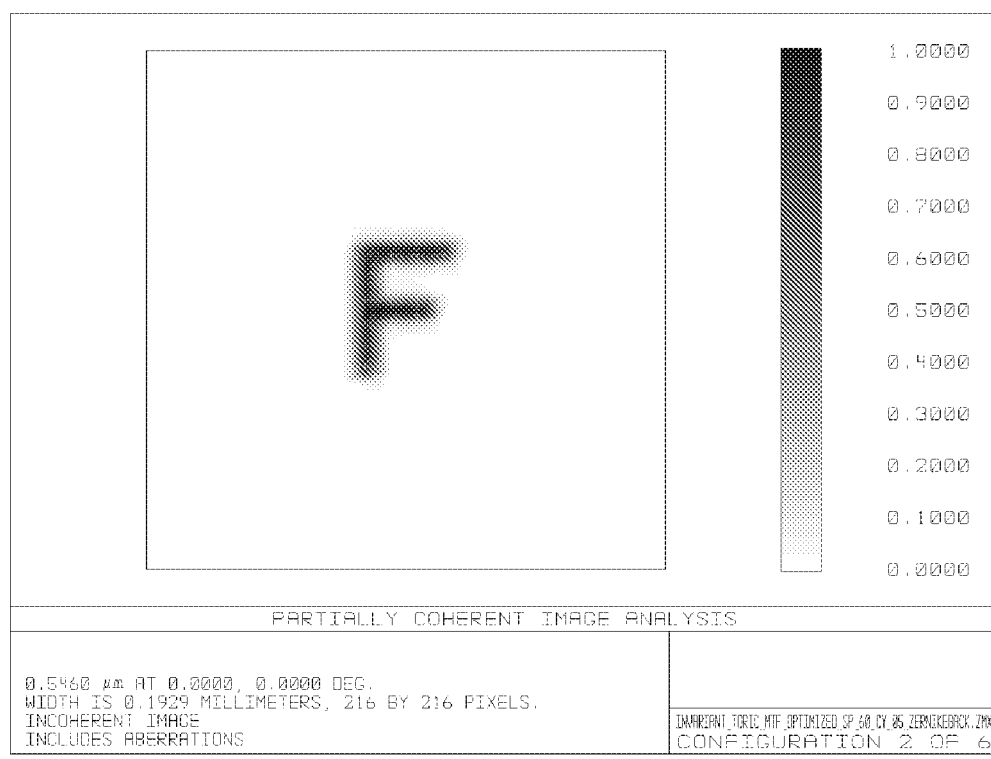
Figure 7E:
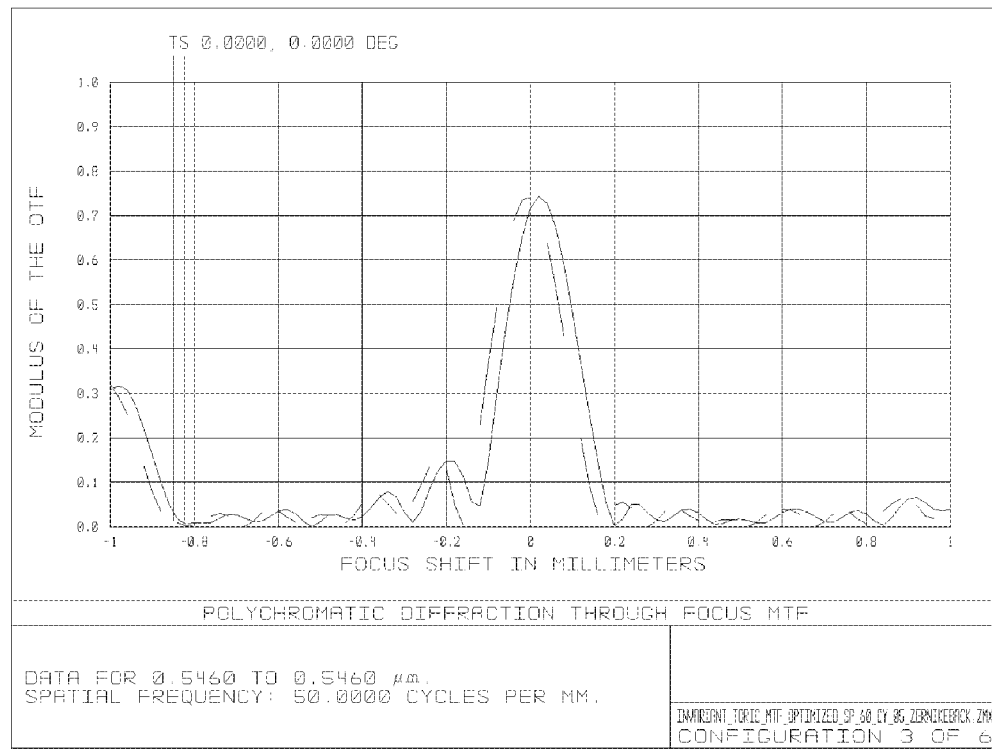
Figure 7F:
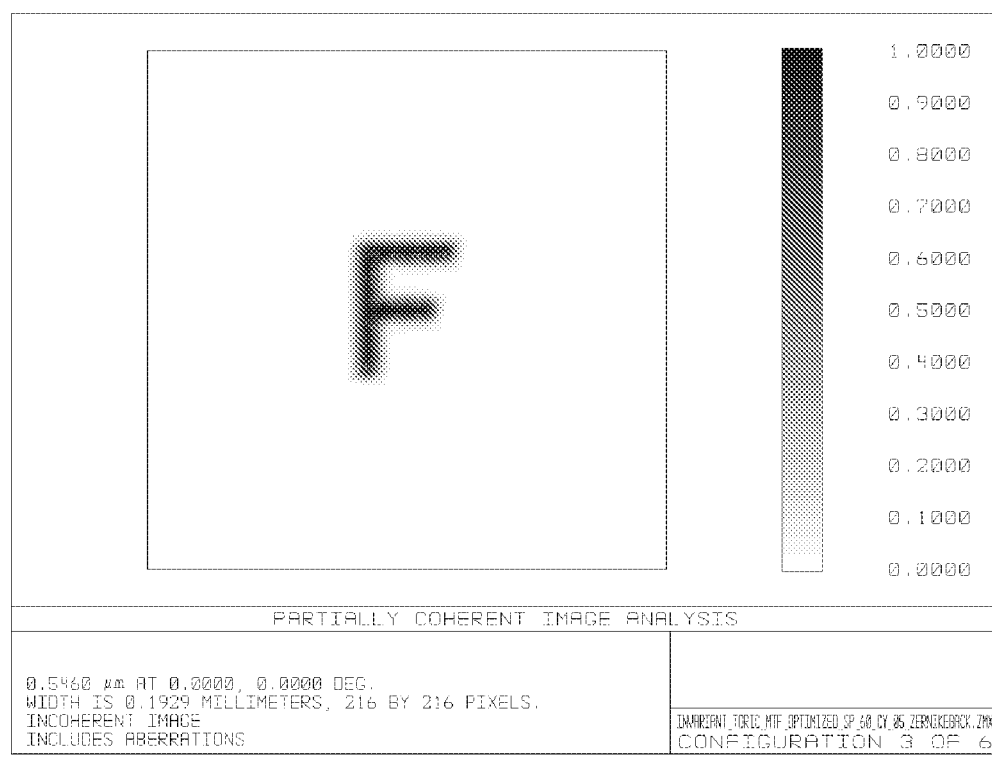
Figure 7G:
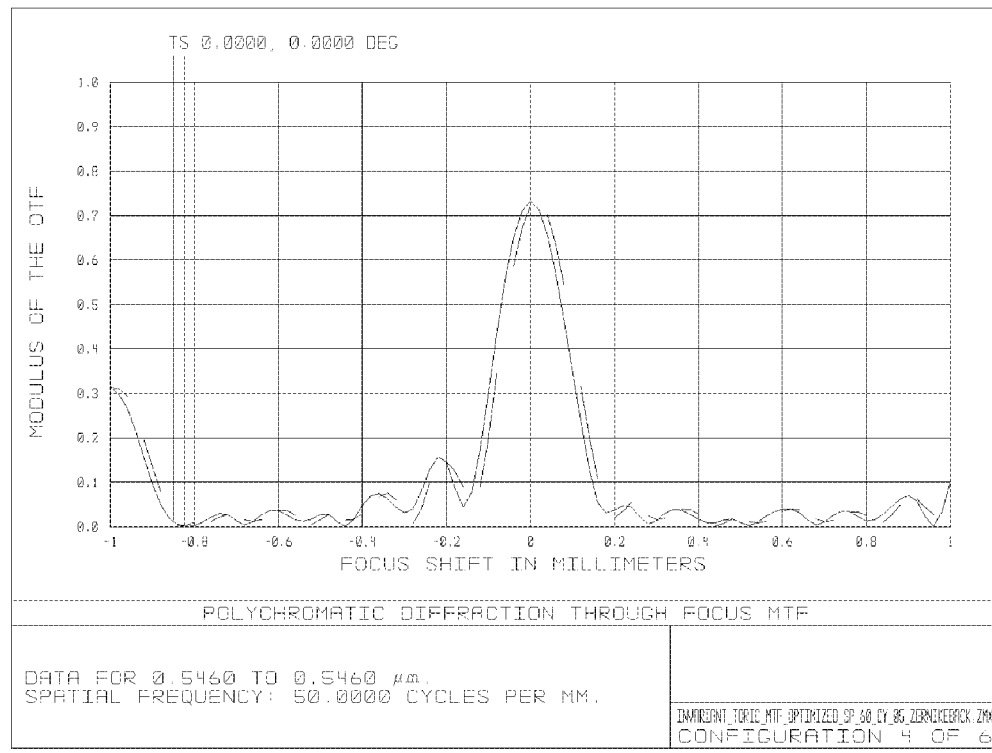
Figure 7H:
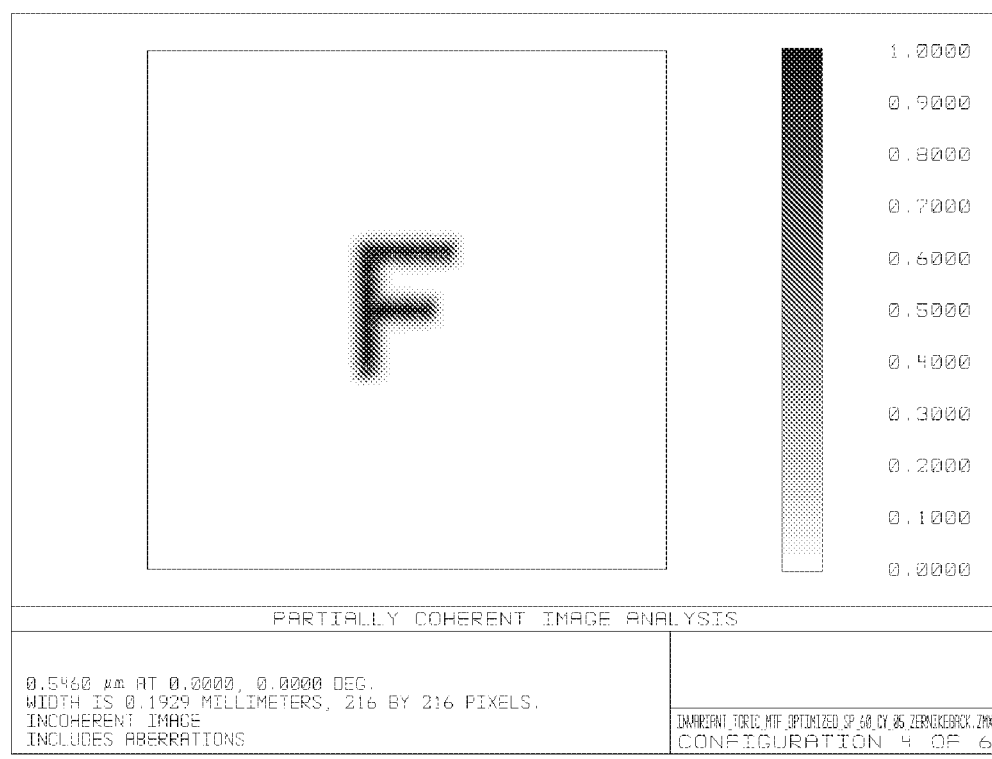
Figure 7I:
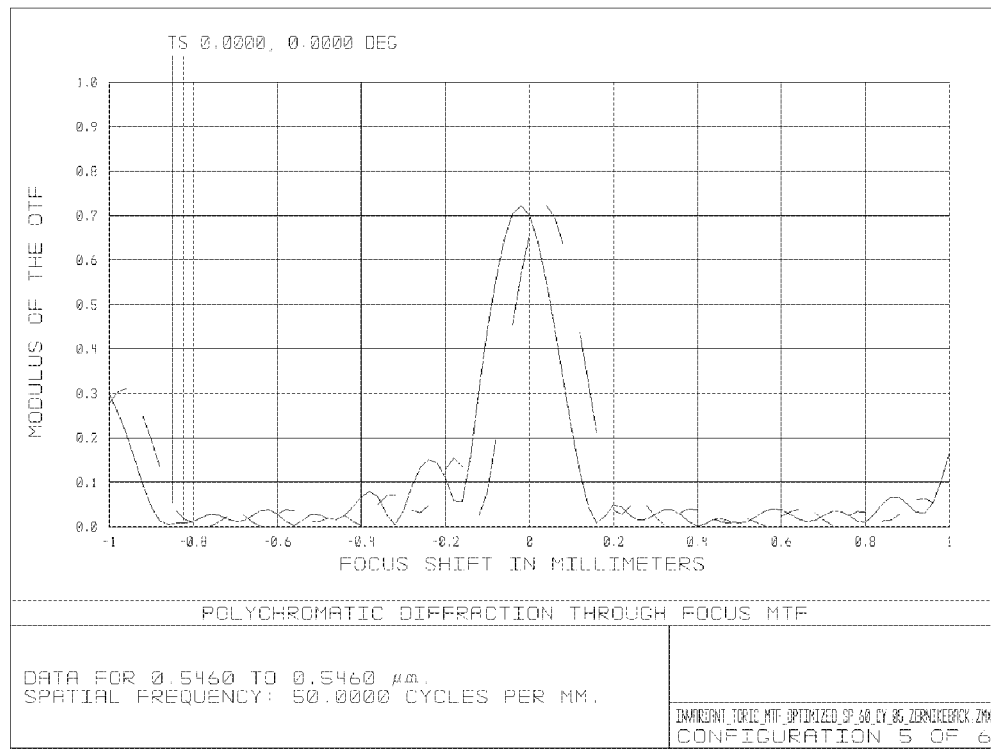
Figure 7J:
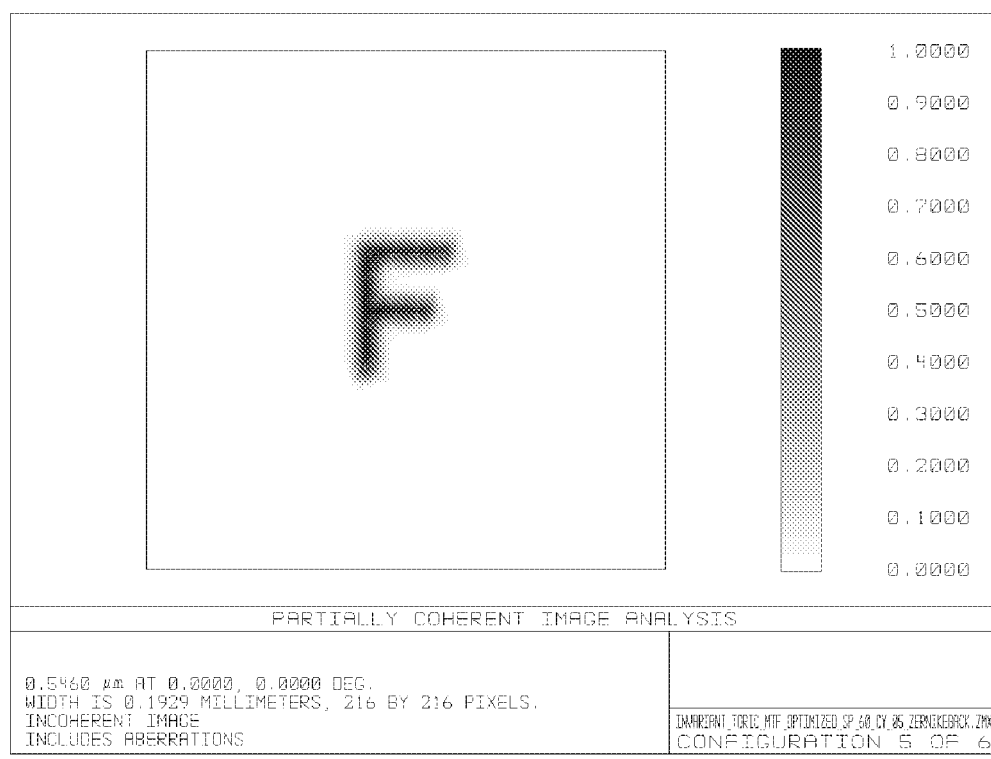
Figure 7K:
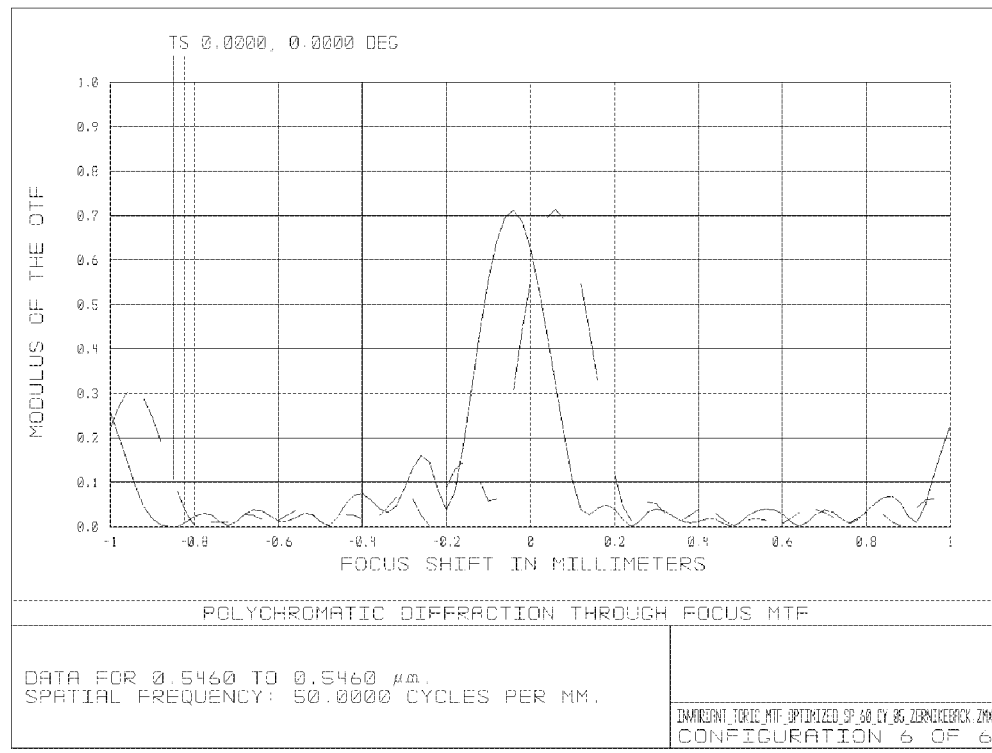
Figure 7L:
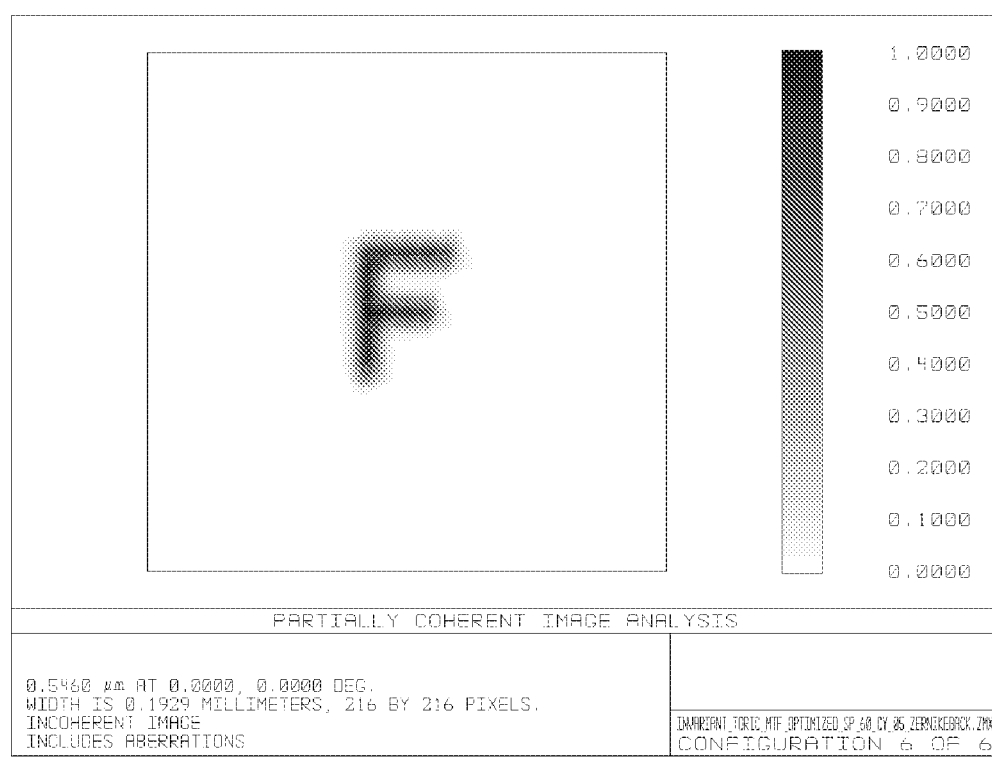
Figure 8:
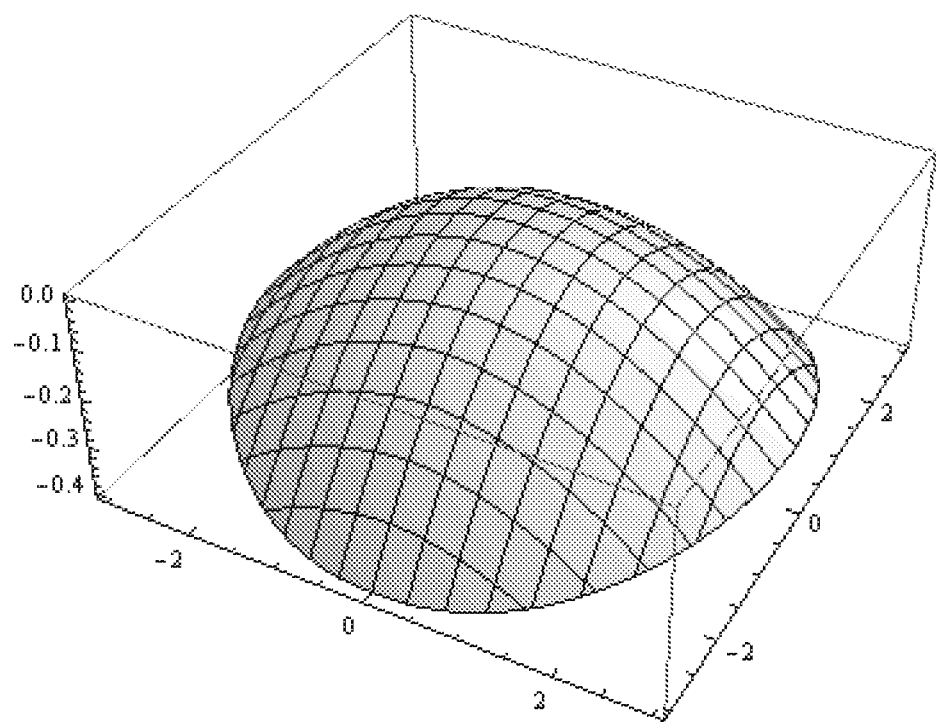
Figure 9:
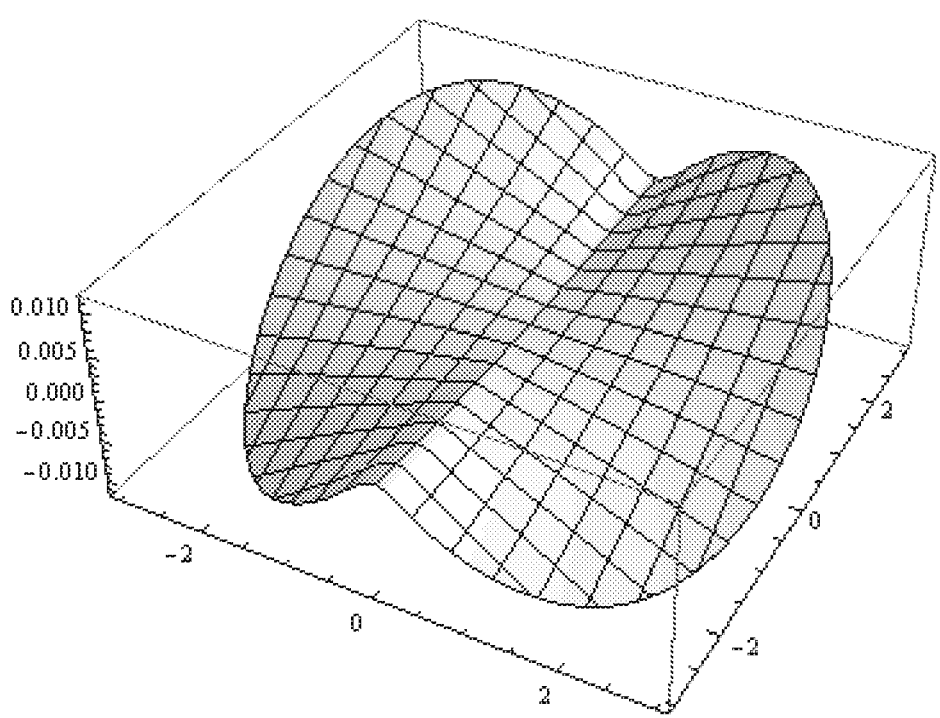
Figure 10:
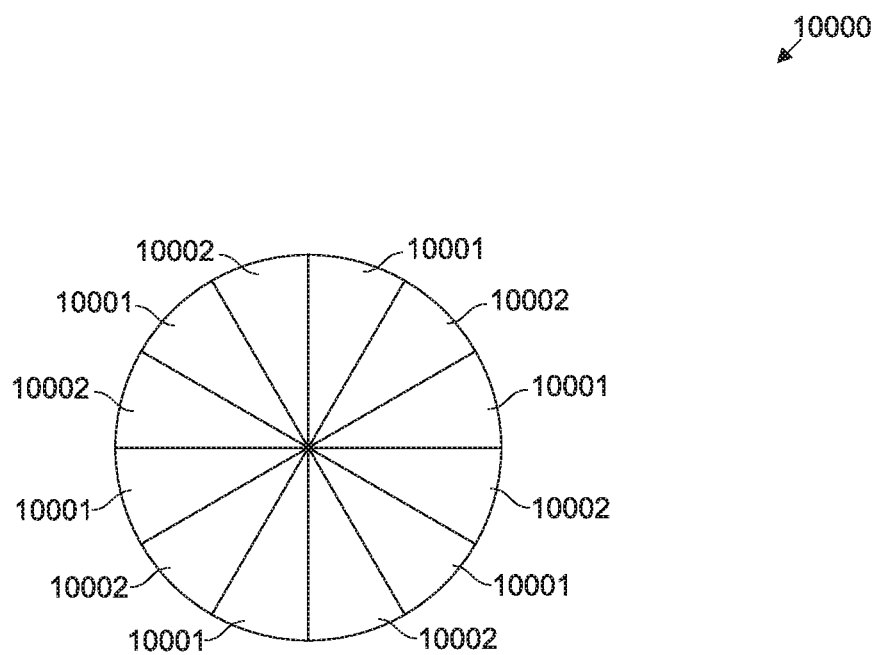
Figure 10:
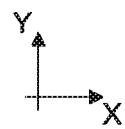
Figure 11:
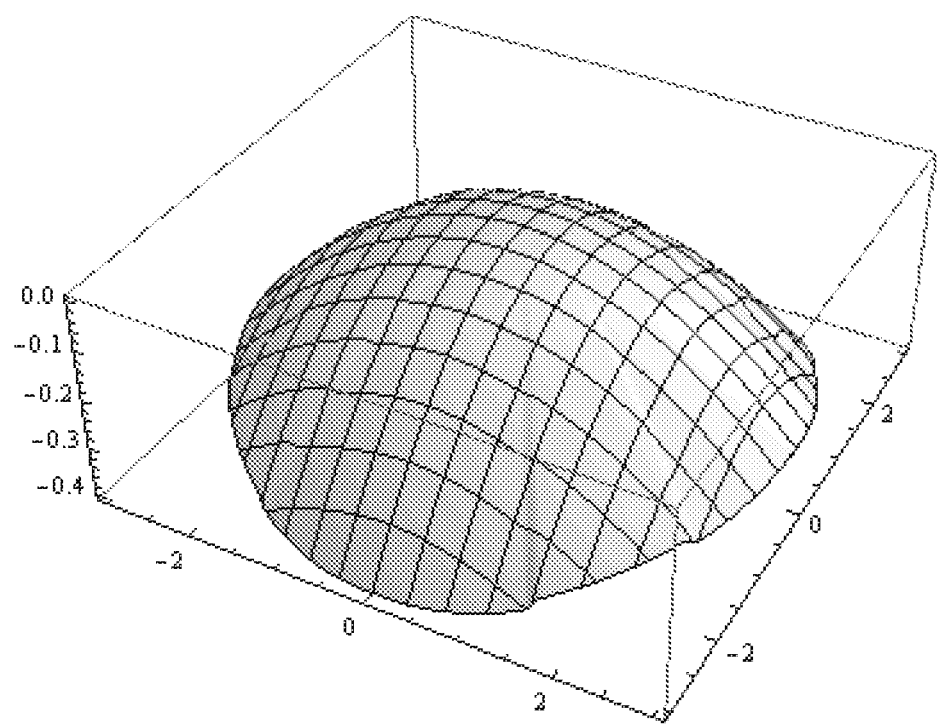
Figure 12:
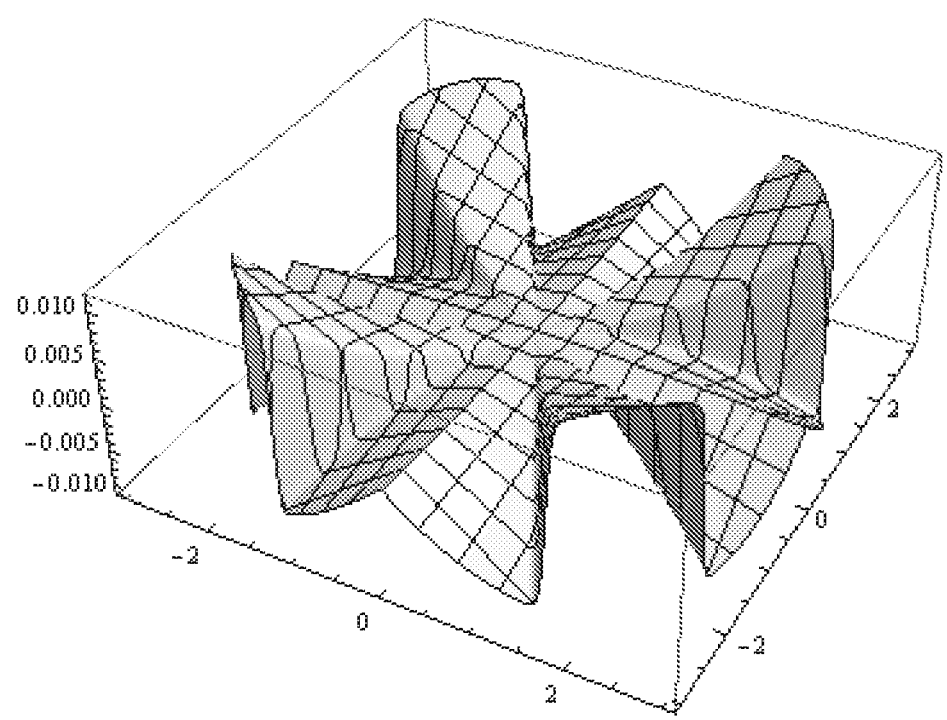

In particular:

FIGS. 1A and 1B diagrammatically depict a front view and a sectional view of a toric lens 1000, respectively;

FIG. 2 diagrammatically depicts the pattern of the power of the toric lens 1000 in FIG. 1A related to a circular section centered on the optical axis and for simplicity normalized so that it is between 0 D and 1 D;

FIG. 3 diagrammatically depicts the misalignment of a toric lens with respect to an ideal correction axis;

FIG. 4 diagrammatically depicts the residual astigmatism caused by a misalignment of a toric lens with respect to the ideal axis;

FIGS. 5A-5L diagrammatically depict measurements of the residual astigmatism effect for a toric lens 1000 in FIG. 1A;

FIG. 6 diagrammatically depicts a front view of a lens 6000 according to an embodiment of the present invention;

FIGS. 7A-7L diagrammatically depict measurements of the residual astigmatism effect for lens 1000 in FIG. 6;

FIG. 8 diagrammatically depicts a front topography of lens 6000 in FIG. 6;

FIG. 9 diagrammatically depicts the topography of the corrective element alone for lens 6000 in FIG. 6;

FIG. 10 diagrammatically depicts a front view of a lens 10000 according to an embodiment of the present invention;

FIG. 11 diagrammatically depicts a front topography of lens 10000 in FIG. 10;

FIG. 12 diagrammatically depicts the topography of the corrective element alone for lens 10000 in FIG. 10.

DETAILED DESCRIPTION OF THE INVENTION

The relationship which expresses the power of a cylindrical lens evaluated at a fixed radius along a meridian varies as a function of the square cosine of the angle which separates said meridian from a reference meridian.

The total power can be represented by the chart shown in FIG. 2. In particular, the chart shows the power "P" of a lens as a function of the separation angle "Ang" between the subject and the reference meridians, expressed in radians.

With the same relationship, it is possible to represent the diagrammatic situation of an eye with astigmatism, for which the correction lens is misaligned. In particular, with reference to FIG. 3, the lens meridian M1 can form an angle $\alpha$ other than zero with the main meridian of corneal astigmatism represented by axis Y. By way of example, FIG. 4 depicts with line 4001 the power of a corneal astigmatism with meridian M1 oriented at an angle $\alpha$ of 45°-5°. Line 4003 represents the astigmatism power of a corrective lens oriented at an angle $\alpha$ with meridian M1 oriented at an angle $\alpha$ of 45°+5°, thus deliberately incorrect with respect to the corneal astigmatism of line 4001. Line 4002 represents the residual astigmatism, not corrected, which expresses the difference between the two powers.

The functional relationship which describes the residual astigmatism can be determined by expressing the corneal aberration and the correction made by the correcting lens with their wavefront.

The expression of the wavefront emerging from the exit pupil of an optical system (including the eye) can be represented by means of a series expansion of Zernike polynoms; in particular, a wavefront in which only the Zernike contributions related to astigmatism appear is given by the following equation:

$$W[\rho, \theta] = 2\sqrt{Z4^2 + Z5^2}\,\rho^2 \text{Cos}\left[\theta - \frac{1}{2}\text{ArcTan}\left[\frac{Z5}{Z4}\right]\right]^2 \quad (1)$$

where Z4 and Z5 are the coefficients referred to the Zernike polynoms $Z_4$ and $Z_5$ (n=2, m=2) which describe the contribution of the cylindrical defect, whereas $\rho$ and $\theta$ are the normalized pupil coordinates. The Zernike polynoms $Z_4$ and $Z_5$ are a function of the normalized pupil radius $\rho$ and of angle $\theta$ as follows:

$$Z_4[\rho,\theta] = Z4\rho^2 \text{Cos}[2\theta]$$

$$Z_5[\rho,\theta] = Z5\rho^2 \text{Sin}[2\theta]$$

In particular, the variation of Z4 and Z5 modifies the orientation of the cylinder axis identified by the angle:

$$\frac{1}{2}\text{ArcTan}\left[\frac{Z5}{Z4}\right]$$

Assuming now that a cylindrical wavefront (generally represented by relationship (1)) is associated with the aberration induced by a cornea with astigmatic defect; in order to compensate for this defect, an equal and opposite contribution will be added to the wavefront, obtained for example by replacing the crystalline lens with an appropriately designed toric intraocular lens. When the axis of the intraocular lens is perfectly aligned with the axis of the cornea, the sum of the two contributions is canceled and the refractive defect is corrected.

In practice, however, it may happen that the two contributions are angularly separated (as a result of a non-perfect positioning of the lens inside the capsular bag) resulting in the correction being only partial.

In order to determine the residual defect due to the partial misalignment of the IOL lens, angle $\alpha$ is introduced in the wavefront expressed by (1), i.e. a further axis rotation of the cylinder, as follows:

$$W_{cornea}[\rho, \theta] = 2\sqrt{Z4^2 + Z5^2}\,\rho^2 \text{Cos}\left[\alpha + \theta - \frac{1}{2}\text{ArcTan}\left[\frac{Z5}{Z4}\right]\right]^2$$

Moreover, in order to simplify the calculation, assuming that the wavefront associated with the intraocular lens is rotated by the same angle $\alpha$ but in the opposite direction (thus $-\alpha$):

$$W_{iol}[\rho, \theta] = 2\sqrt{Z4^2 + Z5^2}\,\rho^2 \text{Cos}\left[\alpha - \theta + \frac{1}{2}\text{ArcTan}\left[\frac{Z5}{Z4}\right]\right]^2$$

By subtracting the two contributions (the corneal astigmatism should be compensated), the total wavefront will be:

$$W = W_{cornea}[\rho, \theta] - W_{iol}[\rho, \theta] ==$$
$$-4\sqrt{Z4^2 + Z5^2}\,\rho^2 \text{Cos}[\alpha]\text{Sin}[\alpha]\left(\frac{Z4\text{Sin}[2\theta]}{\sqrt{Z4^2 + Z5^2}} - \frac{Z5\text{Cos}[2\theta]}{\sqrt{Z4^2 + Z5^2}}\right)$$

A linear combination of Zernike polynoms $Z_4$ and $Z_5$, the amplitude of which is a function of angle $\alpha$. By defining an astigmatism axis $\gamma$ such that $$\mathrm{Cos}[\gamma] = \frac{Z5}{\sqrt{Z4^2 + Z5^2}} \text{ and } \mathrm{Sin}[\gamma] = \frac{Z4}{\sqrt{Z4^2 + Z5^2}}$$

the above relationship becomes:

$$= 4\sqrt{Z4^2+Z5^2}\rho^2 \, \mathrm{Sin}[2\alpha]\mathrm{Cos}[\gamma+2\theta]$$

where the constant term Sin[2α] is recognizable, which modulates the amplitude thereof.

Figure 5A:
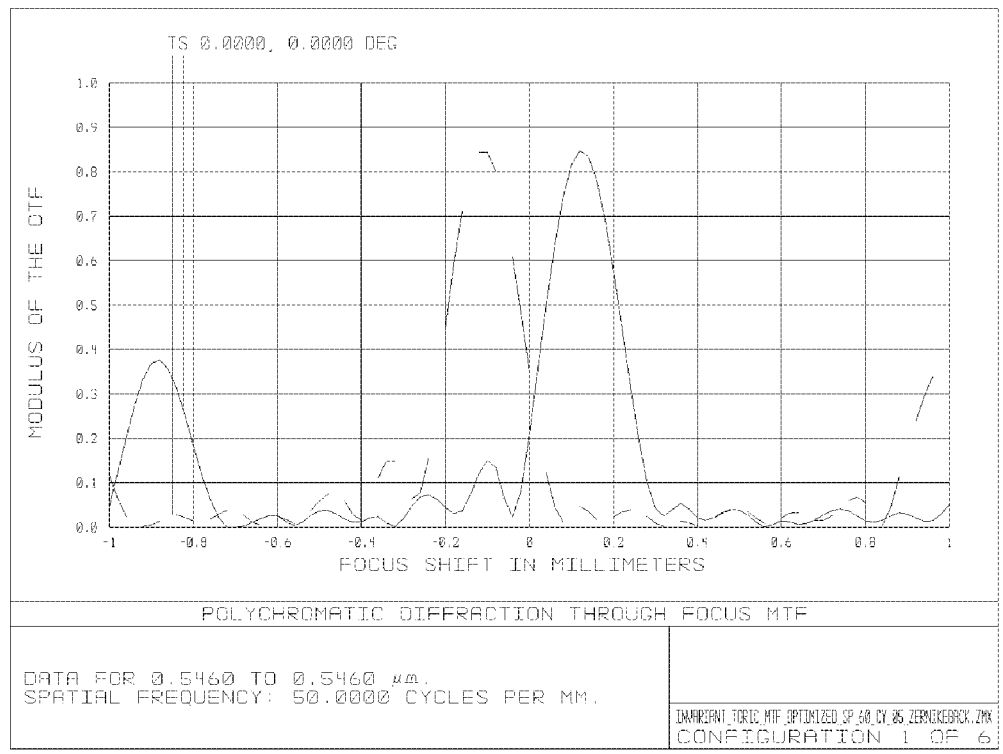
Figure 5B:
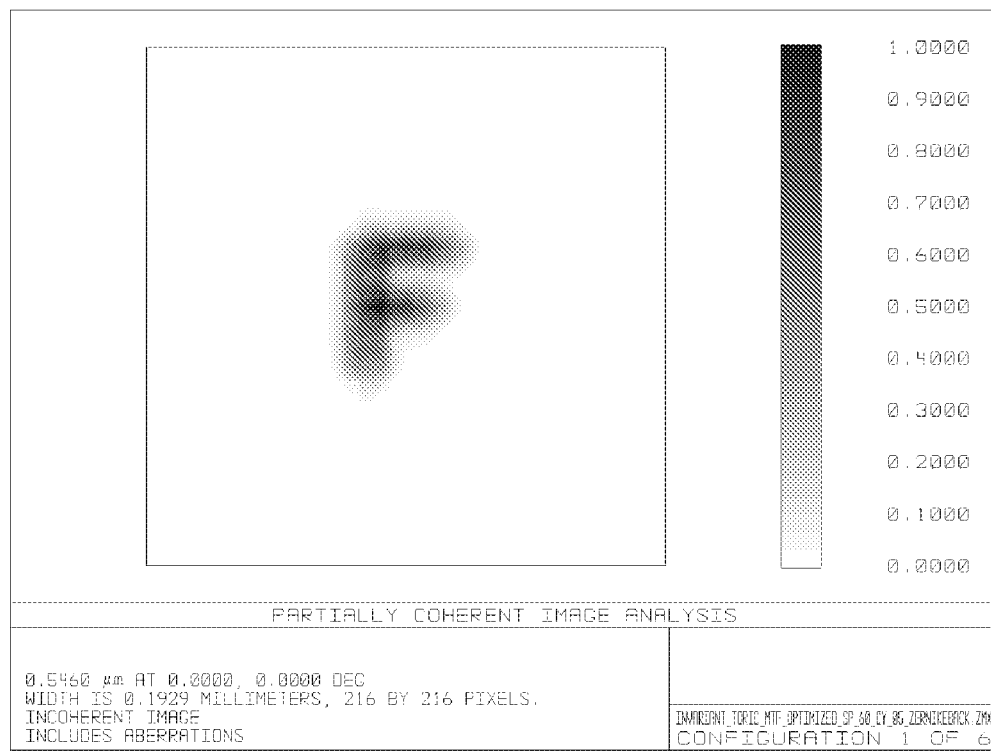
Figure 5C:
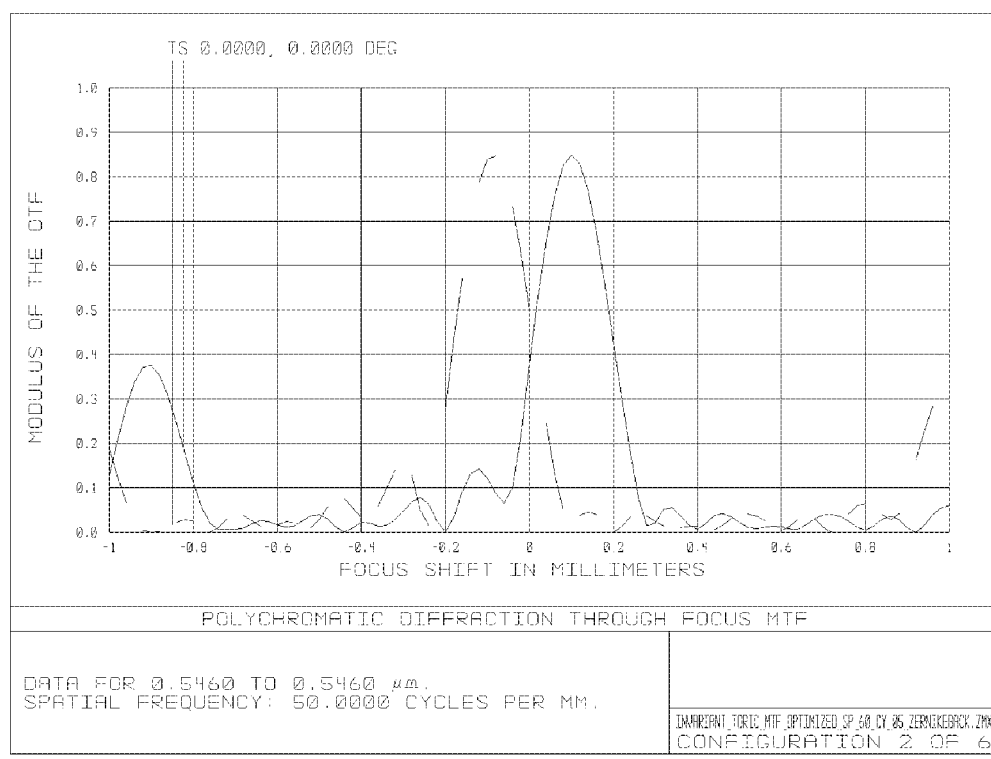
Figure 5D:
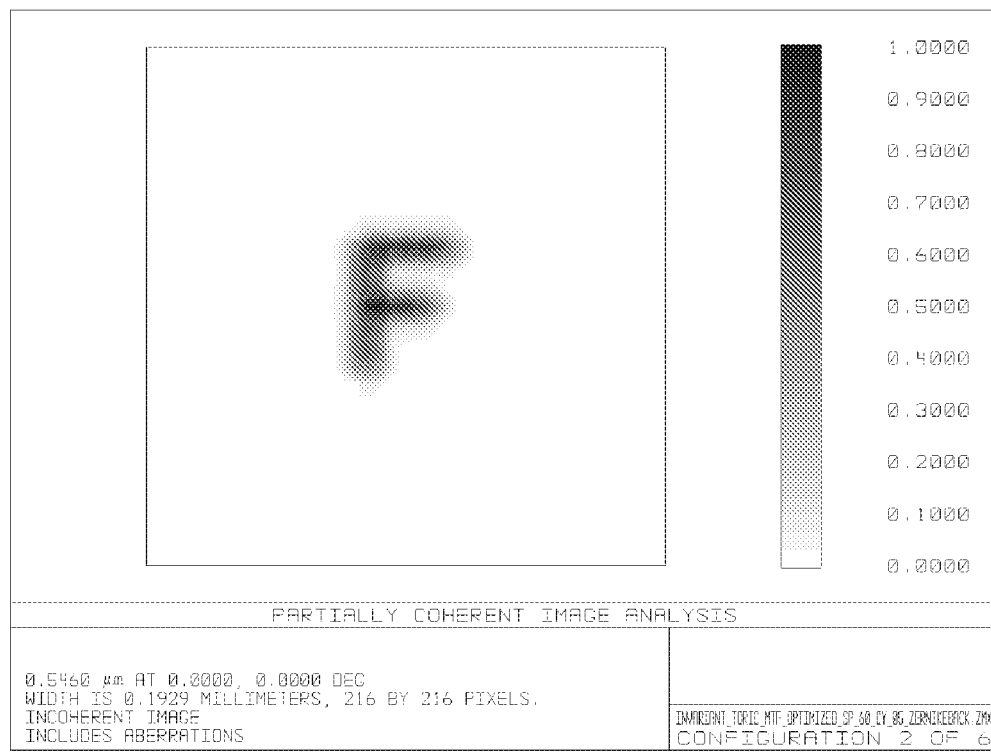
Figure 5E:
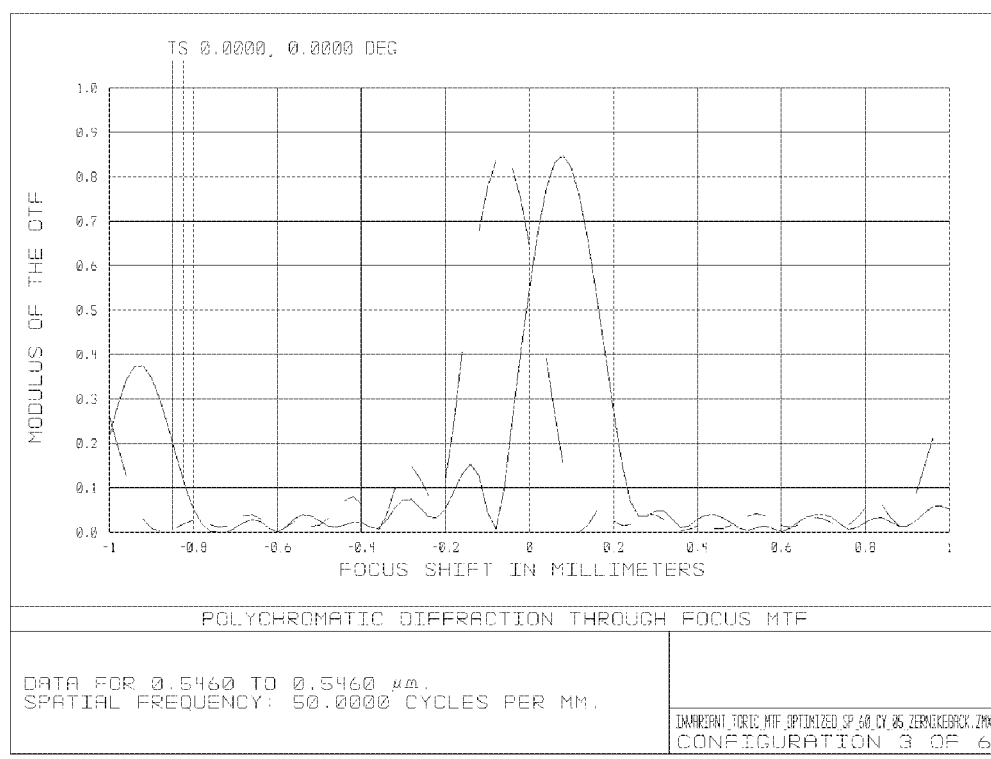
Figure 5F:
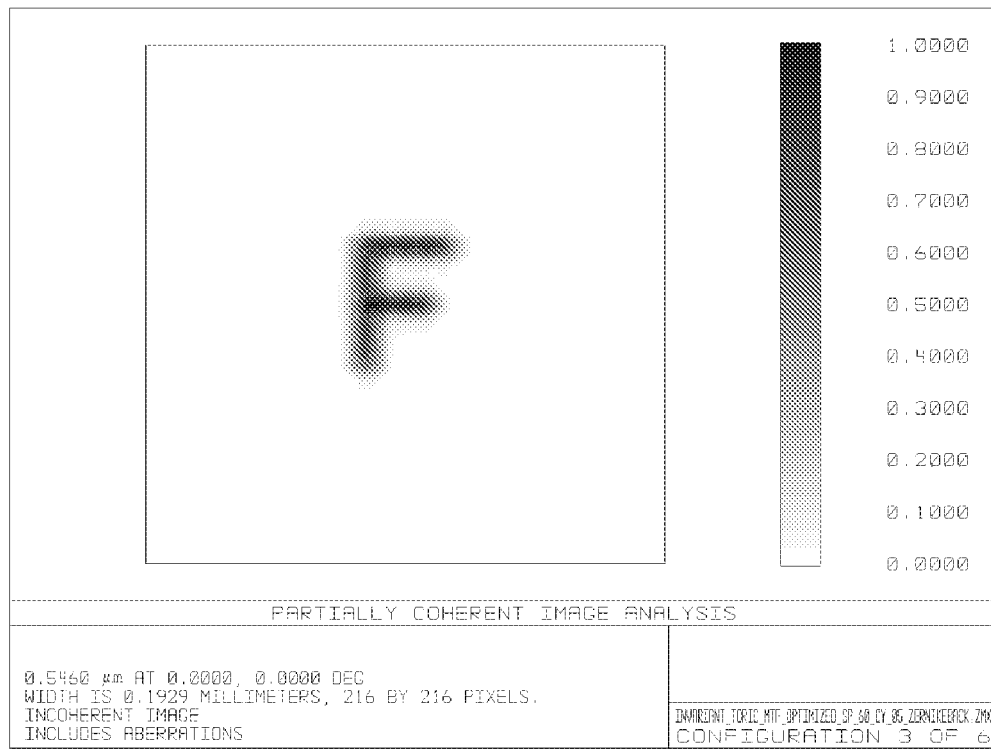
Figure 5G:
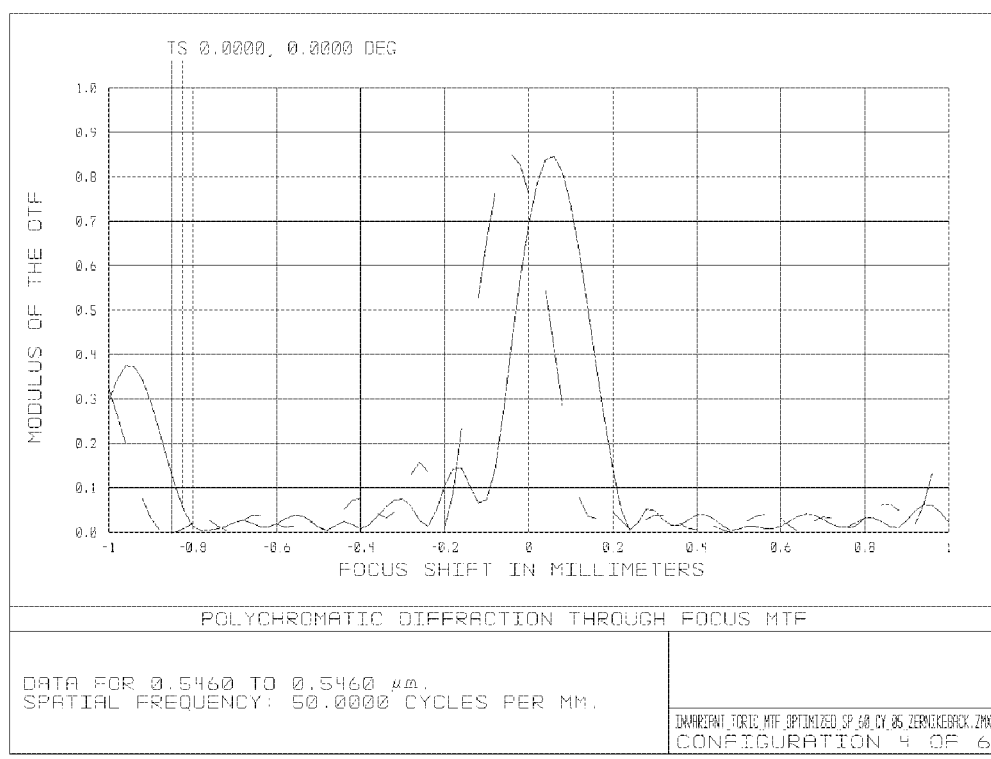
Figure 5H:
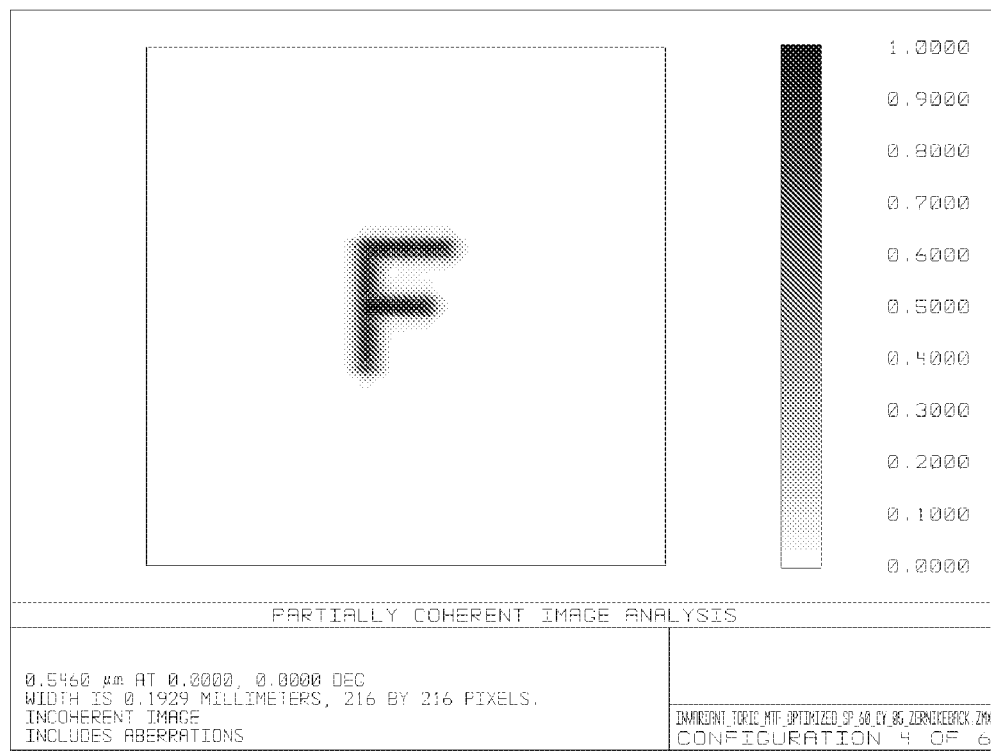
Figure 5I:
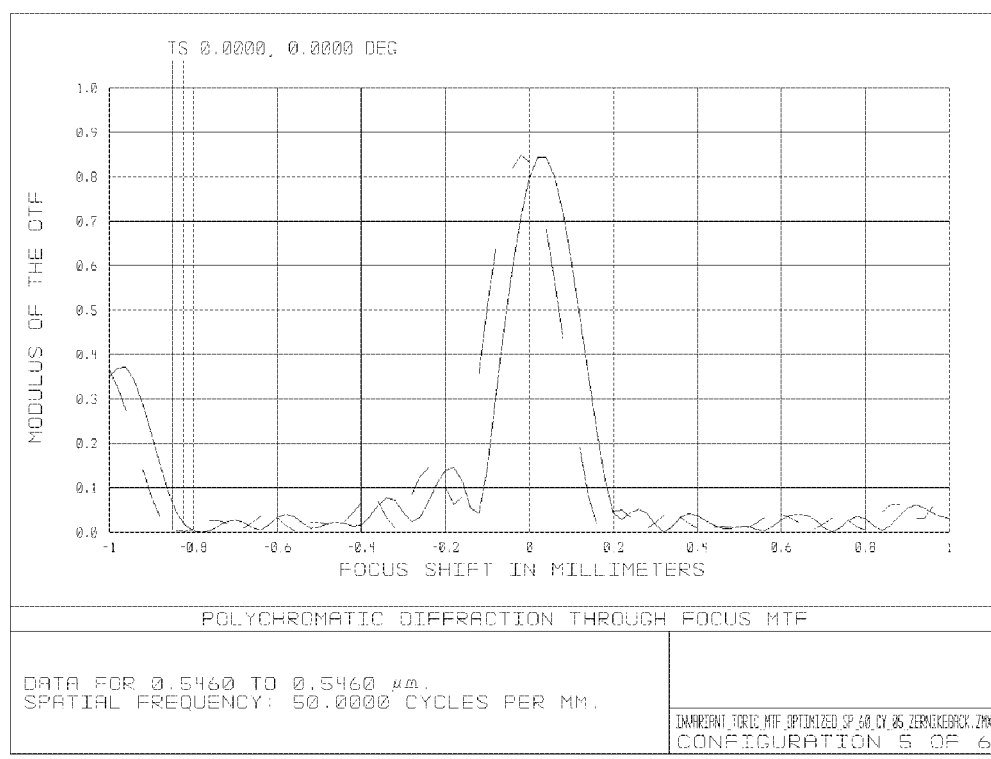
Figure 5J:
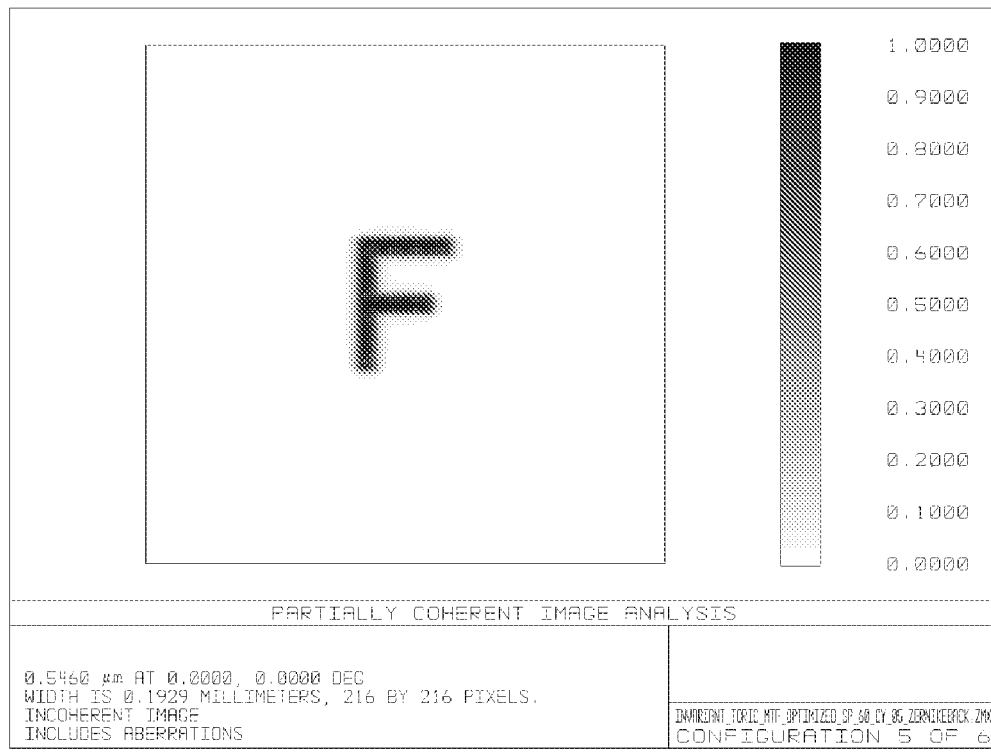
Figure 5K:
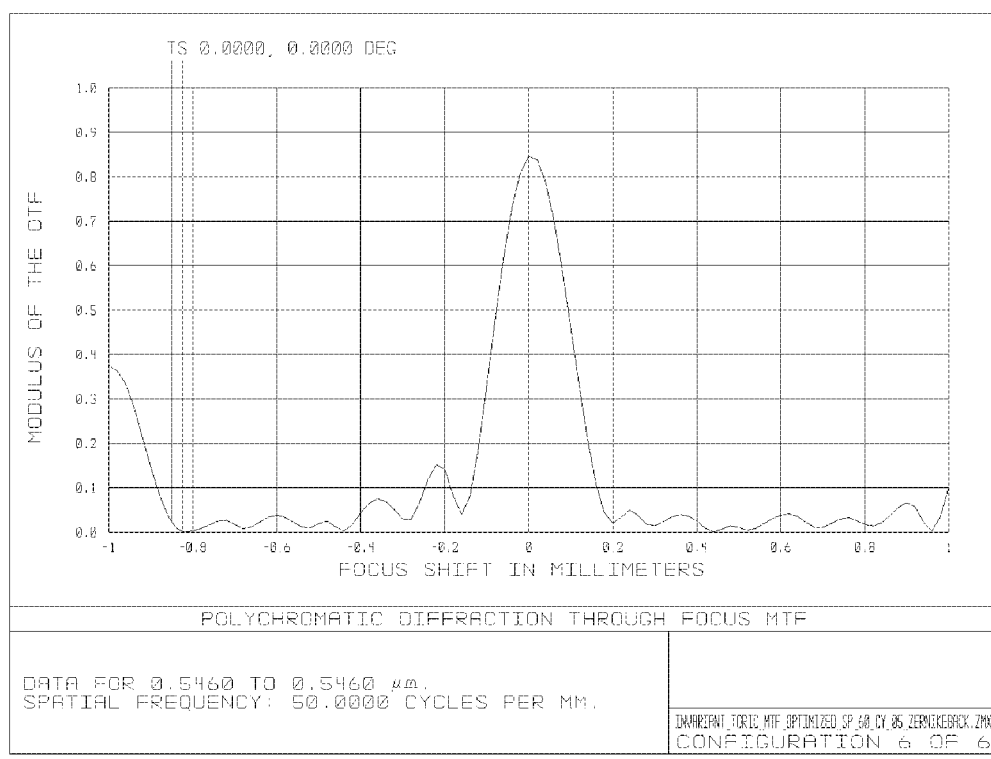
Figure 5L:
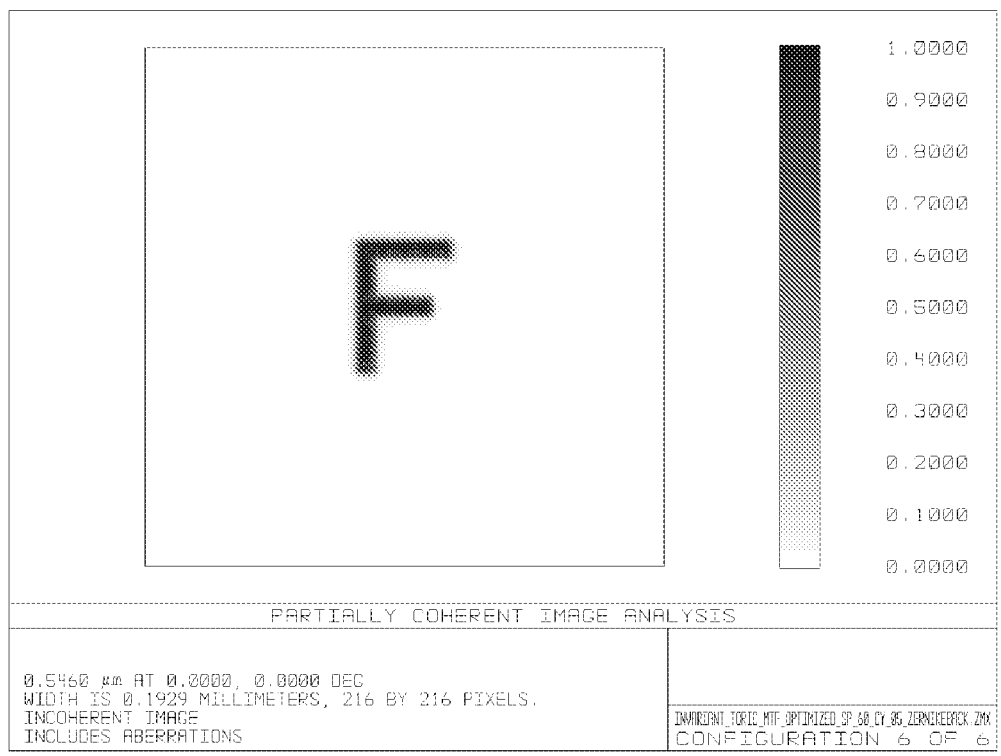

Since the optical power is defined as the average of the main curvatures of the wavefront, it follows that the residual astigmatism, i.e. the difference between the two powers—the corneal and the misaligned lens powers—is proportional to the relationship:

$$\mathrm{Cos}[2\theta]\cdot\mathrm{Sin}[2\alpha] \tag{Eq. 1}$$

where θ indicates the position of a radius or meridian to which the correction is applied, with respect to the reference meridian, whereas α indicates the misalignment angle of lens 1000 with respect to the corneal surface or, in other words, with respect to the ideal astigmatism correction angle. In the example described above, α is of 5 degrees, for example. The misalignment leads to a reduction in the lens correction. By way of example, FIGS. 5A-5L diagrammatically show the Modulation Transfer Function or MTF, also known as Optical Transfer Function Module, and the analysis of retinal images expressed in 50 cyc/mm as a function of angle α, in an example in which the pupil has a diameter of 3 mm. Specifically, FIGS. 5A-5L show the pattern of MTF for a toric lens 1000 and the orientation α of the toric lens is varied with respect to the cornea in steps of 2° so as to verify how it deteriorates. In FIGS. 5A and 5B, the misalignment is maximum and corresponds to 10 degrees; in FIGS. 5C and 5D it is 8 degrees; in FIGS. 5E and 5F it is 6 degrees; in FIGS. 5G and 5H it is 4 degrees; in FIGS. 5I and 5J it is 2 degrees; finally, in FIGS. 5K and 5L, the misalignment is minimum and corresponds to 0 degrees.

In the images showing the MTF, a line corresponds to the tangential MTF whereas the other to the sagittal MTF. In a perfectly astigmatism-corrected eye, the sagittal and tangential MTFs coincide. However, if the lens is rotated and therefore the main meridian thereof is misaligned from the main meridian of the cornea, the two MTFs split due to the presence of residual astigmatism.

As shown in FIGS. 5A and 5B, with α of 10 degrees, thus in the case of maximum separation considered, letter F appears blurred and the MTF in the position of best focus is about 0.2. By aligning lens 1000 with respect to the cornea with greater precision, thereby decreasing angle α, the image quality progressively improves, as can be seen from the evolution in FIGS. 5B-5L. In particular, in FIG. 5K, the MTF reaches a value slightly greater than 0.8 in the position of best focus.

In one embodiment of the present invention, a deformation is introduced on the front or back surface of the lens, i.e. on the same surface on which the toric lens is obtained or on the opposite surface, such a deformation being obtained by adding an additional surface consisting of the combination of the two Zernike polynoms $Z_4$ and $Z_5$ to the existing surface, so that the resulting wavefront variation is equal and opposite to the contribution of residual astigmatism indicated in the above equation:

$$\mathrm{Cos}[2\theta]\cdot\mathrm{Sin}[2\alpha] \tag{Eq. 1}$$

Subtracting this contribution to the overall eye wavefront actually makes the optical system more tolerant to small rotations of the lens itself.

As can be seen from the chart in FIG. 4, the corrective term 4002 corresponds to a cylindrical deformation of the lens which is translated by a degrees from the main meridian of the cylindrical base surface which determines the variation 4003 of the corrective lens power. The residual power due to the incorrect positioning, i.e. the rotation, of the lens with respect to the cornea is thus compensated by adding a cylindrical surface to the cylindrical base surface of the lens which is rotated, with respect to the first one, by an angle α.

However, when the main meridian of the lens is rotated by an angle −α with respect to the main meridian of the cornea, the sign of the corrective term is reversed; therefore, the cylindrical deformation introduced on the lens will not correct the defect anymore.

For this reason, the lens surface is divided into two substantially symmetrical sections 6001 and 6002, as shown in FIG. 6. In the embodiment shown, the division takes place along the main meridian of the lens. However, the invention is not limited to this case and each meridian can be used to divide the lens into two parts. It will also be apparent that the division does not need to be made by a meridian and that the two parts are exactly 50% of the lens. In some cases, one of the two parts will be larger than the other, for example to accommodate manufacturing tolerances.

A corrective cylindrical surface is made on part 6001, which corrects the defect when the lens is rotated by an angle α. A corrective term is therefore made on part 6002, which corrects the defect when the lens is rotated by the opposite angle −α Thereby, the overall behavior of the lens is deteriorated with respect to a basic toric lens which corrects astigmatism, positioned perfectly in axis with the cornea, but is more tolerant to small variations, in particular within ±α° of rotation.

In other words, the correction is equal to $$\mathrm{Cos}[2\theta]\cdot\mathrm{Sin}[2\alpha] \tag{Eq. 1}$$

in part 6001, and $$\mathrm{Cos}[2\theta]\cdot\mathrm{Sin}[-2\alpha] \tag{Eq. 2}$$

in part 6002.

With this embodiment, it is possible to obtain a toric lens 6000 with an advantageous correction behavior with respect to the possible misalignments α in both positive and negative directions.

In particular, in fact, as can be seen in FIGS. 7A-7L, lens 6000 improves the visual quality, recognizable by the higher MTF value than the basic toric lens when rotated, the behavior of which is shown in FIGS. 5A-5L. Specifically, FIGS. 7A-7F diagrammatically show the MTF expressed in 50 cyc/mm as a function of angle α, in an example in which the pupil has a diameter of 3 mm for lens 6000.

As can be seen, the MTF value is now between 0.6 and 0.7, with an obvious improvement of the image quality for high separations, as for example in the case of a equal to 10 degrees, without having a high deterioration for low separations, for example close to a equal to 0 degrees.

FIG. 8 diagrammatically shows a front topography of lens 6000.

The axes are both measured in millimeters.

As described above, in the left-hand part of the lens in the figure, a deformation is applied which corrects the cylinder to −α degrees. In the right-hand part in the figure, a correction is applied which corrects the cylinder to +α degrees. The corrective contribution introduces a different deformation on the two halves which is such as to produce a very small discontinuity in the coupling area. As can be seen in the figure, such a discontinuity is practically unnoticeable, especially when compared to the scale of the lens itself. In the case in the figure, the lens has an aperture having a diameter of 6 mm, as shown in FIG. 8.

FIG. 9 diagrammatically depicts the topography of the corrective element alone for lens 6000, i.e. the difference between lens 6000 and a conventional toric lens. The axes are both measured in millimeters. As can be seen, the deviations from the standard toric surface are very small, as they are of the order of 10 µm. This allows the above-described correction to be integrated in any type of lens without particular drawbacks related to a possible significant increase in the lens thickness. It can also be seen in the chart that the correction has a substantially symmetrical behavior on the two right and left halves.

Moreover, the correction has a substantially sinusoidal pattern around the rotation axis Z, which is particularly advantageous because such a pattern can easily be implemented with common manufacturing equipment.

Alternative Embodiment

In the above embodiment, the lens is divided into two parts which are substantially similar. However, as detailed above, the invention is not limited to this case and the two parts can have different dimensions.

In addition, the number of parts is not limited to two but can be any number, not necessarily even. By way of example, in a further embodiment of the present invention shown in FIG. 10, lens 10000 is conceptually made by interspersing 12 sectors 10001 and 10002, a half of which has a correction similar to that of part 6001, respectively, whereas the other half has a correction similar to that of part 6002, respectively.

FIG. 11 diagrammatically depicts a front topography of lens 10000, whereas FIG. 12 diagrammatically depicts the topography of the corrective element alone for lens 10000.

The deformation introduced on the lens by the correction factor, shown in FIG. 12, introduces deviations with respect to the surface of the lens without correction, which are very small being of the order of 10 µm. Therefore, also in this case, the thickness variation introduced by the correction is substantially irrelevant with respect to the thickness of the lens, as shown in FIG. 11.

Generally, the lens can be divided in any number of parts. The discontinuities thus generated on the lens surfaces are small, as described above. However, in large numbers, they can generate a deterioration in vision. There is therefore an upper limit on the number of parts in which the lens can be divided. Generally, it will be preferred not to considerably increase the number of subdivisions so as to avoid a decrease of the Modulation Transfer Function value and a corresponding deterioration of vision.

Numerical Examples

In all the embodiments described above, the magnitude of the correction depends on angle α. It is therefore not possible to precisely correct the residual astigmatism for each value of α. However, an average value of α may be selected in the range of possible movement of the lens.

In some embodiments, therefore, the possible maximum rotation angle of the lens will be evaluated and α will be selected as half the maximum possible angle.

The inventors have experimentally found that, in many practical cases, a rotation value in the range from 0 to 20 degrees, preferably from 0 to 15 degrees, even more preferably from 0 to 10 degrees, can be considered as valid, in particular for an intraocular lens. In this case, the value of α can be smaller than or equal to 10 degrees, preferably smaller than 7.5 degrees, even more preferably smaller than or equal to 5 degrees, respectively. In any case, the rotation value will advantageously be larger if the lens is intended to be applied to cases with larger rotations. By way of example, for a contact lens where the rotation angle is larger because of the movement imparted by the eyelids, an angle α smaller than 30 degrees may be considered, preferably smaller than 20 degrees, even more preferably smaller than 10 degrees. Conversely, in cases where the rotation is small, for example for an eyeglass lens where the rotation is limited by the presence of the frame, α may be smaller than or equal to 6 degrees, preferably smaller than or equal to 4 degrees, even more preferably smaller than or equal to 2 degrees, respectively.

In the above description, reference is made to a general lens. The numerical examples shown in FIGS. 5A-5L, 7A-7L, 8, 9, 11 and 12 advantageously relate to a lens having compatible dimensions with those of an intraocular lens. However, the invention is not limited to this case and can be implemented in the form of an intraocular lens, IOL, contact lens or eyeglass lens.

In the above description, various embodiments are independently described, so as to facilitate the understanding thereof. However, it will be apparent to those skilled in the art that the present invention is not limited to the single embodiments described. Conversely, such embodiments and/or even just some features of each embodiment may be combined together to obtain new embodiments of the present invention as defined by the claims.

REFERENCE NUMERALS

1000: lens
R1: curvature radius
M1: meridian
R2: curvature radius
M2: meridian
α: misalignment angle
4001: power of a corneal astigmatism
4002: residual astigmatism
4003: astigmatism power of a corrective lens
6000: lens
6001: lens part
6002: lens part
10000: lens
10001: lens part
10002: lens part

The invention claimed is:

1. A toric lens for correction of an astigmatism, said toric lens comprising:
   a front surface and a back surface, at least one of said front surface and said back surface being divided into plural interspersing sectors,
   and having a deformation described by a linear combination of Zernike polynoms Z4 and Z5, said deformation resulting in a power correction factor proportional to the term of $\text{Cos}[2\theta] \text{Sin}[2\alpha]$,
   wherein θ indicates a position of a meridian to which the correction is applied, with respect to a reference meridian (M1) of the toric lens,
   wherein α indicates a misalignment angle of the toric lens with respect to an ideal correction angle of the astigmatism, said correction factor being applied on a first half and on a second half of said interspersing sectors, and having opposite signs on adjacent ones of said sectors.

2. The lens according to claim 1, wherein the interspersing sectors have substantially a same dimension.

* * * * *